(12) United States Patent
Acevedo-Duncan et al.

(10) Patent No.: US 8,461,192 B2
(45) Date of Patent: Jun. 11, 2013

(54) METHOD OF SELECTIVELY INHIBITING PKCIOTA

(75) Inventors: Mildred Acevedo-Duncan, Plant City, FL (US); Shraddha R. Desai, Tampa, FL (US); Hla Yee Win, Tampa, FL (US); David A. Ostrov, Gainesville, FL (US); Prajit P. Pillai, Tampa, FL (US); Diondra D. Hill, Tampa, FL (US)

(73) Assignees: The University of South Florida, Tampa, FL (US); The United States of America Department of Veterans Affairs, Washington, DC (US); The University of Florida Research Foundation, Inc., Gainesville, FL (US)

( * ) Notice: Subject to any disclaimer, the term of this patent is extended or adjusted under 35 U.S.C. 154(b) by 585 days.

(21) Appl. No.: 12/210,576

(22) Filed: Sep. 15, 2008

(65) Prior Publication Data

US 2009/0075932 A1 Mar. 19, 2009

Related U.S. Application Data

(60) Provisional application No. 60/993,814, filed on Sep. 13, 2007.

(51) Int. Cl.
*A01N 43/50* (2006.01)
*A01N 43/52* (2006.01)
*A61K 31/415* (2006.01)

(52) U.S. Cl.
USPC ............................ 514/385; 514/393; 514/396

(58) Field of Classification Search
USPC .................................. 514/51, 385, 393, 396
See application file for complete search history.

(56) References Cited

U.S. PATENT DOCUMENTS

| | | | |
|---|---|---|---|
| 3,328,261 A | 6/1967 | Kiyoshi Nakayama | |
| 4,575,498 A | 3/1986 | Holmes et al. | |
| 5,082,829 A | 1/1992 | Gruber et al. | |
| 5,595,902 A | 1/1997 | Biden et al. | |
| 5,672,746 A * | 9/1997 | Nau et al. | 562/598 |
| 5,728,707 A | 3/1998 | Wehrmann | |
| 5,777,100 A | 7/1998 | Bullough et al. | |
| 2004/0014049 A1 | 1/2004 | Cowsert et al. | |
| 2004/0023901 A1 | 2/2004 | Cook et al. | |
| 2005/0233987 A1 | 10/2005 | Lopez Blanco et al. | |
| 2006/0216730 A1 | 9/2006 | Plowman et al. | |

FOREIGN PATENT DOCUMENTS

| | | |
|---|---|---|
| JP | 59025390 | 2/1984 |
| JP | 3198790 | 8/1991 |
| WO | 9202213 A1 | 2/1992 |
| WO | 01/44497 A2 | 6/2001 |
| WO | 2004/041212 A2 | 5/2004 |

OTHER PUBLICATIONS

Schmitt et al. ("Enantiospecific Synthesis of Carbocyclic Aminoimidazole Carboxamide Ribonucleotide (C-AICAR), Succinoaminoimidazole Carboxamide Ribonucleotide (C-SAICAR), and a New Intermediate for SAICAR Analogs" Nucleosides & Nucleotides, 14 (9&10), 1929-1945, 1995).*

Messerschmidt et al. "Crystal Structure of the Catalytic Domain of Human Atypical Protein Kinase C-iota Reveals Interaction Mode of Phosphorylation Site in Turn Motif." J. Mol. Biol., 2005. vol. 352. pp. 918-931.

Minana M.D., V. Felipo, and S Grisolia. "Differential Effects of the Protein Kinase C Inhibitors H7 and Calphostin C on the Cell Cycle of Neuroblastoma Cells." Brain Research. vol. 596. Issue.1-2. 1992. pp. 157-62.

Bettayeb K, et al. "Meriolins, a New Class of Cell Death Inducing Kinase Inhibitors with Enhanced Selectivity for Cyclin-Dependent Kinases." Cancer Research. vol. 67. Issue 17. 2007. pp. 8325-8334.

Guerreiro A.S., et al. "Protein Kinase B Modulates the Sensitivity of Human Neuroblastoma Cells to Insulin-Like Growth Factor Receptor Inhibition." International Journal of Cancer. Journal International Du Cancer. vol. 119. Issue.11. 2006. pp. 2527-2538.

Cattaneo M.G., et al. "A Somatostatin Analogue Inhibits MAPinase Activation and Cell Proliferation in Human Neuroblastoma and in Human Small Cell Lung Carcinoma Cell Lines." FEBS Letters. vol. 397. Issue.2-3. 1996. pp. 164.

* cited by examiner

*Primary Examiner* — Yong Chong
(74) *Attorney, Agent, or Firm* — Saliwanchik, Lloyd & Eisenschenk (57) ABSTRACT

PKCiota inhibitor 1H-imidazole-4-carboxamide, 5-amino-1-[2,3-dihydroxy-4-[(phosphonooxy)methyl]cyclopentyl]-, [1R-(1α,2β,3β,4α)], (ICA-1), targets a unique sequence (amino acid residues 469-475) in the catalytic domain of PKCiota and inhibits PKCiota activity. The data shows suprising and unexpected ability of ICA-1 to selectively inhibit the proliferation of cells that overexpress PKCiota.

6 Claims, 5 Drawing Sheets

METHOD OF SELECTIVELY INHIBITING PKCIOTA

CROSS REFERENCE TO RELATED APPLICATIONS

This application is a Nonprovisional Application of co-pending U.S. Provisional Application No. 60/993,814 filed Sep. 13, 2007, which is incorporated herein by reference.

BACKGROUND OF THE INVENTION

Neuroblastomas are highly lethal tumors and 85% of cerebral neuroblastoma occurs in children and 15% in adults. Neuroblastoma is the fourth most commontype of cancer in children. According to the American Cancer Society, there are approximately 650 new cases of neuroblastoma each year in the United States.

Neuroblastoma (neuro: nerve and blastoma: cancer) has its origin in the sympathetic nervous system: the network of nerves transmitting neuronal messages originating in the brain to the various parts of the body. The primary site of the tumor is one of the adrenal glands; however, it may also occur in other tissues like abdomen, pelvis, neck or spinal cord. Neuroblastomas are highly lethal tumors and 85% of cerebral neuroblastoma occurs in children and 15% in adults. Neuroblastoma is the fourth most common type of cancer in children and the most common in babies. As per the statistics of the American Cancer Society, about 650 new cases of neuroblastoma are diagnosed each year in the United States. The intensity of neuroblastoma lies in its primary target; infants and small children. Thus, justifying the importance of increased research to find apotential cure for the disease.

Cells are normally subjected to strict regulatory mechanisms that limit cell division. Protein kinases and protein phosphorylation are the central dogmas that control the entry and passage of cells through the cell cycle. Cancer is the outcome of abnormalities in these mechanisms that lead to unchecked cell division.

Protein kinase C (PKC) family of Ser/Thr kinases are involved in transmembrane signal transduction pathways triggered by various extra and intracellular stimuli. They are involved in the control of various cellular responses like proliferation and differentiation, gene expression and tumor promotion. There are 11 known isoforms of the PKC family which are found in varying amounts in the cytosolic and membrane fractions of cells, and this ratio is constitutive of the type of tissue.

The PKC isozymes can be classified into three groups. Group I (classical PKCs) includes the $Ca^{2+}$ and DAG (diacylglycerol) dependent isozymes: PKC-α, PKC-βI, PKC-βII and PKC-γ. Group II (novel PKCs) includes the $Ca^{2+}$ independent isozymes: PKC-δ, PKC-ε, PKC-η and PKC-θ. Group III (atypical PKCs) includes the $Ca^{2+}$ and DAG independent isozymes: PKCiota, PKCzeta and PKC-μ (protein kinase D).

SUMMARY OF INVENTION

Here, the inventors report the identification of PKCiota inhibitor 1H-imidazole-4-carboxamide, 5-amino-1-[2,3-dihydroxy-4-[(phosphonooxy)methyl]cyclopentyl]-,[1R-(1α,2β,3β,4α)], (ICA-1), that targets a unique sequence (amino acid residues 469-475) in the catalytic domain of PKCiota and inhibits PKCiota activity. The data shows suprising and unexpected ability of ICA-1 to selectively inhibit the proliferation of neuroblastoma cells that overexpress PKCiota.

Therefore, in a first embodiment, the invention includes a method of treating a neoplastic condition by administering a therapeutically effective amount of a compound which selectively inhibits protein kinase C-iota (PKCiota). The therapeutically effective compound of this embodiment binds to a unique amino acid sequence (amino acid residues 469-475) of the catalytic domain of PKCiota. The unique amino acid sequence of a particular embodiment is glutamine-isoleucine-arginine-isoleucine-proline-arginine-serine.

In another embodiment, the invention includes a method of treating a neoplastic condition by administering a therapeutically effective amount of a 1H-imidazole-4-carboxamide, 5-amino-1-[2,3-dihydroxy-4-phosphonooxy)methyl]cyclopentyl]-[1R-(1α,2β,3β,4α)] (ICA-1), which selectively binds to a unique amino acid sequence of the catalytic domain of PKCiota. The therapeutically effective amount of an illustrative embodiment is between about 40 nM and 100 nM. The compound is administered about every 24 hours to enhance efficacy.

In yet another embodiment, the invention includes a method of selectively inhibiting the expression of protein kinase C-iota (PKCiota) in a cell by contacting the cell with a therapeutically effective amount of a compound that binds to a unique amino acid sequence of the catalytic domain of PKCiota. The therapeutically effective compound of this embodiment binds to a unique amino acid sequence (amino acid residues 469-475) of the catalytic domain of PKCiota. The unique amino acid sequence of a particular embodiment is glutamine-isoleucine-arginine-isoleucine-proline-arginine-serine.

The invention also includes a method of selectively inhibiting the expression of protein kinase C-iota (PKCiota) in a cell by contacting the cell with a therapeutically effective amount of 1H-imidazole-4-carboxamide, 5-amino-1-[2,3-dihydroxy-4-phosphonooxy)methyl]cyclopentyl]-[1R-(1α,2β,3β,4α)] (ICA-1), which selectively binds to a unique amino acid sequence of the catalytic domain of PKCiota. The therapeutically effective amount of an illustrative embodiment is between about 40 nM and 100 nM. The compound is administered about every 24 hours to enhance efficacy.

BRIEF DESCRIPTION OF THE DRAWINGS

For a fuller understanding of the invention, reference should be made to the following detailed description, taken in connection with the accompanying drawings, in which:

FIG. 3. PKC Kinase activity assay. ICA-1(10 μM or 50 μM) drug was added with PKCiota or PKCzeta pure enzymes in 200 μl of kinase buffer for 5 min at 30° C. to detect phosphorylation of MBP. (A) is a western blot analysis of PKC kinase activity, PKCiota, PKCzeta, MBP and pMBP were immunoblotted and incubated with antibodies specific to the antigens. (B) shows the densitometry demonstrating a decrease in PKC kinase activity. Comparison of controls with the 10 μM ICA-1 treatment showed that there was a significant difference with P values of only PKCiota ($P<0.005$) and not PKCzeta. Similarly, comparison of the 50 μM ICA-1 incubation demonstrated significant difference with PKCiota ($P<0.002$).

FIG. 5. ICA-1 reduced the expression of PKCiota in BE(2)-C: BE(2)-C cells were cultured (1.5×105) in 75 cm2 tissue culture flasks For Single ICA-1 treatment, twenty-four hours post plating, fresh media was supplied and cells were incubated with either equal volume of sterile water (vehicle control) or ICA-1 (80 nM). For Multiple ICA-1 treatment, twenty four hour post plating fresh media was supplied and cells were incubated with either equal volume of sterile water (vehicle control) or ICA-1 (80 nM). This was followed by addition of ICA-1 (80 nM) every twenty four hours. Total cell-lysates were prepared over a time period of 24, 48 and 72 hour and these were subjected to Western blot analysis for PKCiota. (B) The intensity of each band was measured by the Scion Image program (Scion Corporation, Frederick, Md., USA). The band intensities of samples treated with with ICA-1 were normalized against samples treated with pure water (vehicle control). The data shows significant reduction in PKCiota on ICA-1 treatment (P value<0.05)

FIG. 6. Effect of ICA-1 on PKCiota in presence of the proteasome inhibitor MG 115: BE(2)-C cells were cultured (1.5×105) in 75 cm2 tissue culture flasks. For Single ICA-1 treatment, twenty-four hours post plating, fresh media was supplied and cells were incubated with either equal volume of sterile water (vehicle control) or ICA-1 (80 nM) and MG 115 (350 nM). For Multiple ICA-1 treatment, twenty four hour post plating fresh media was supplied and cells were incubated with either equal volume of sterile water (vehicle control) or ICA-1 (80 nM) and MG 115 (350 nM). This was followed by addition of ICA-1 (80 nM) every twenty four hours. Total cell-lysate were prepared over a time period of 24, 48 and 72 hour and these were subjected to Western blot analysis for PKCiota Cells were cultured ($5×10^4$) in 25 cm2 tissue culture flasks. Twenty-four hours post plating, fresh media was supplied and cells were incubated with either equal volume of sterile water (vehicle control) or ICA-1 (40 nM to 100 nM). Cell viability was determined over a time period of 24, 48 and 72 hour using trypan blue exclusion assay (P value<0.05)

DETAILED DESCRIPTION OF THE PREFERRED EMBODIMENT

Figure 1:
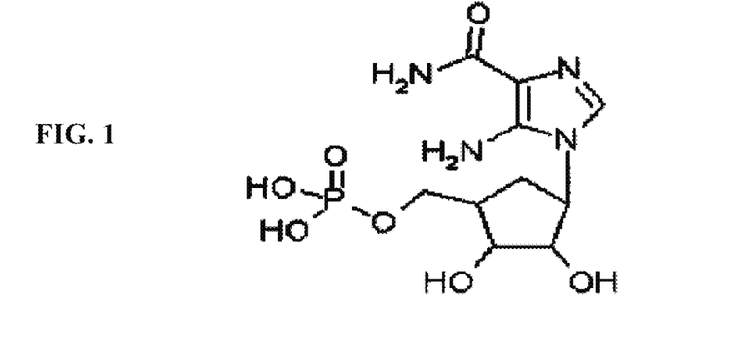
FIG. 1. The chemical formula of ICA-1.

The invention includes methods that selectively inhibit cellular proliferation associated with neoplastic conditions further associated with overexpression of PKCiota. The inventors show suprising results when ICA-1 (1H-imidazole-4-carboxamide, 5-amino-1-[2,3-dihydroxy-4-phosphonooxy)methyl]cyclopentyl]-[1R-(1α,2β,3β,4α)]), FIG. 1, is administered to neoplastic cells which overexpress PKCiota over PKCzeta (which shows 84% homology in the catalytic domain thereof).

Here the inventors show unexpected results relating to the specificity of compounds targeted to the catalytic domain of PKCiota. Specifically, compounds such as ICA-1 inhibit PKCiota by binding to a unique amino acid sequence in the catalytic domain. Accordingly, these results also extend to other compounds that selectively bind to the disclosed sequence of the catalytic domain.

Here, the inventos demonstrate the specificity and effectiveness of ICA-1 in prevention of cell-proliferation of neoplastic conditions, as shown in the neuroblastoma cell line BE(2)-C. The decrease in proliferation correlates with the decrease in PKCiota levels. The IC50 for ICA-1 is 80 nM, however, multiple administrations (every 24 hour) had increased effect in downregulation of PKCiota.

ICA-1 treatment was performed in presence of the proteosome inhibitor MG115 to establish the involvement of the ubiquitin-proteosome pathway in regulating PKCiota. The results show that the downregulation of PKCiota on ICA-1 treatment was independent of the ubiquitin-proteosome pathway.

Among the PKC family, PKCiota shares the highest degree of homology with PKCzeta. Overall amino acid sequences for both the atypical PKCs are 72% identical. Of greater significance, the homology with regard to the catalytic domain shows 84% homology. This near identity highlights the difficulty in designing an inhibitor specific for just one of the atypical isoforms. Thus, the specificity of ICA-1 for the atypical PKCiota over PKCzeta, and the low dose requirement of ICA-1 present surprising an unexpected results of using ICA-1 as an anticancer compound.

The compounds of this invention can be used in diagnostics, therapeutics, prophylaxis, and as research reagents and in kits. Since the compounds of this invention bind to an amino acid sequence unique to PKCiota, sandwich, calorimetric and other assays can easily be constructed to exploit this fact. Furthermore, since the compounds of this invention bind specifically to amino acids of the catalytic domain of PKCiota, such assays can be devised for screening of cells and tissues for particular PKCiota isozymes. Such assays can be utilized for diagnosis of diseases associated with PKCiota. Provision of means for detecting binding with PKCiota can routinely be accomplished. Such provision may include enzyme conjugation, radiolabelling or any other suitable detection systems. Kits for detecting the presence or absence of PKCiota may also be prepared.

The present invention is also suitable for diagnosing neoplastic conditions in tissue or other samples from patients suspected of having a neoplastic condition such as neuroblastoma. The ability of the compounds of the present invention to inhibit cell proliferation may be employed to diagnose such states. A number of assays may be formulated employing the present invention, which assays will commonly comprise contacting a tissue sample with a compound of the invention under conditions selected to permit detection and, usually, quantitation of such inhibition. In the context of this invention, to "contact" tissues or cells with a compound means to add the compound(s), usually in a liquid carrier, to a cell suspension or tissue sample, either in vitro or ex vivo, or to administer the compound(s) to cells or tissues within an animal. Similarly, the present invention can be used to distinguish PKC-associated tumors, particularly tumors associated with PKCiota, from tumors having other etiologies, in order that an efficacious treatment regime can be designed.

As used herein, the term "neoplastic condition" refers to a class of diseases characterized by the uncontrolled growth of aberrant cells, whether such condition is characterized as malignant, benign, soft tissue or solid tumor. Specific neoplastic conditions include digestive and gastrointestinal cancers, such as anal cancer, bile duct cancer, gastrointestinal carcinoid tumor, colon cancer, esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; CNS cancer; leukemia and melanoma. In a preferred embodiment, the term "neoplastic condition" refers to neuroblastoma.

Thus, in the context of this invention, a "therapeutically effective amount" is the amount of the compound which is required to have a therapeutic effect. This amount, which will be apparent to the skilled artisan, will depend upon the type of subject, the age and weight of the subject, the type of disease to be treated, perhaps even the gender of the subject, and other factors which are routinely taken into consideration when treating a subject with a disease. A therapeutic effect is assessed in the subject by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor

EXAMPLES

It is understood that modifications which do not substantially affect the activity of the various embodiments of this invention are also included within the definition of the invention provided herein. Accordingly, the following examples are intended to illustrate but not limit the present invention.

Example I

ICA-1 Binds to Unique a PKCiota Amino Acid in the Catalytic Domain

The inventors screened compounds that would bind to and inhibit a unique sequence in the catalytic domain of PKCiota. The unique sequence targeted (SEQ. ID. No. 1) was amino acid residues 469-475 (glutamine-469, isoleucine-470, arginine-471, isoleucine-472, proline-473, arginine-474, serine-475). Molecular docking demonstrated the binding of ICA-1 to amino acid residues 469-475.

The National Cancer Institute/Developmental Therapeutics Program (NCI/DTP) maintains a repository of 139,644 samples (the plated compound set). The three-dimensional coordinates for the NCI/DTP plated compound set in the MDL sd format was converted to the mol2 format by the program SDF2MOL2 (UCSF). Partial atomic charges for the ligands were calculated using SYBDB (UCSF) and added to the plated compound set mol2 file.

The procedure for molecular docking involves: 1) selection of structural pockets in PKCiota suitable for interactions with drug-like small compounds, and 2) molecular docking simulations where each one of approximately 300,000 small compounds (MW<500) is positioned in the selected structural pocket and scored based on predicted polar (e.g., H bond) and non-polar (e.g. Van der Waal's) interactions. The top 30 scoring compounds for each selected structural pocket were obtained for use in functional assays. Docking calculations were performed with the Oct. 15, 2002 development version of DOCKv5.1.0. molecular docking calculations The coordinates for the crystal structure PKC, PDB code 1ZRZ, was used. The molecular surface of the structure was explored using sets of spheres to describe potential binding pockets. The spheres literally fill in the available pocket spaces where a ligand might be able to form a complex. DOCK uses the spheres as a guide to search for orientations of each compound that fit into the selected sites. The sites selected for molecular docking were defined using the SPHGEN/SITE-SELECTOR programs and filtered through the CLUSTER program. The SPHGEN program generates an unbiased grid of points that reflect the actual shape of the selected site. The CLUSTER program groups the selected spheres to define the points that are used by DOCK to match (superimpose) potential ligand atoms with spheres. Twenty-two (22) spheres were used to define the PKCiota site for molecular docking. Each compound in the NCI/DTP repository was positioned in the selected site in 1000 different orientations. Intermolecular AMBER energy scoring (vdw+columbic), contact scoring and bump filtering were implemented in DOCKv5.1.0. PYMOL was used to generate molecular graphic images. All molecular docking jobs were performed on a high performance supercomputer at the University of Florida running linux.

Example II

Role of PKCiota in Proliferation of Neuroblastoma Cells

ICA-1 was synthesized and purchased from Southern Research Institute (Birmingham, Ala.). ICA-1 was dissolved in sterile distilled water (vehicle) before use. BE(2)-C neuroblastoma cells were obtained from the American Tissue Culture Collection (Rockville, Md.) (ATCC # CRL-2268).

Cells were cultured (2×106) and grown as monolayer in 75 cm2 tissue culture flasks until they were 70-80% confluent. Cells were maintained at 37° C. in a humidified atmosphere comprised of 5% CO2. The composition of the complete growth medium was 90% by volume of 1:1 mixture of Eagle's Minimum Essential Medium (EMEM, ATCC 30-2003) and Ham's F12 Medium, 10% fetal bovine serum (FBS), and 5% antibiotics.

Figure 2:
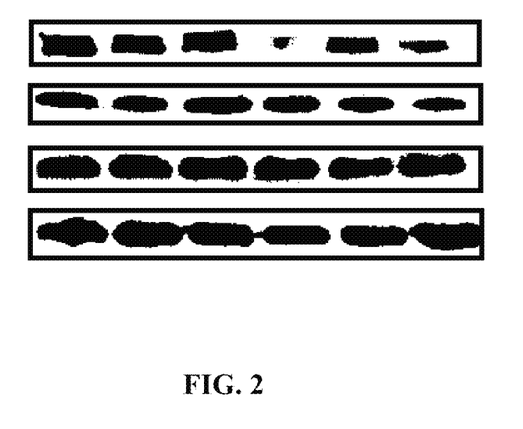
FIG. 2. Role of atypical PKC isoforms in cell proliferation of BE(2)-C cells. Total cell lysates from 50% confluent and serum starved (100% confluent cells were serum starved for 48 hours) BE(2)-C cell-lysate were subjected to Western blot analysis to determine the role of PKCiota and PKCzeta in cell-proliferation.

Total cell lysates from 50% confluent and 100% confluent (serum starved) BE (2)-C cell-lysate were subjected to Western blot analysis to determine the role of PKCiota (FIG. 2) and PKCzeta (FIG. 2) in cell-proliferation. There was significant reduction (P=0.045) in the levels of PKCiota in the starved cells when compared to actively proliferating cells. The above data suggested that the decrease in cell proliferation on starvation could be due to decrease in the expression of PKCiota. As a control, there was no reduction in Caspase-7 indicating that the cells were no undergoing apoptosis. β-actin was used as control to ensure that equal amount of protein was loaded.

Example III

ICA-1 Inhibits PKCiota Induced Phosphorylation of Myelin Basic Protein

A PKC activity assay was performed by suspending 0.01 μg/μl of PKCiota and PKCzeta pure enzyme (Upstate, Charlottesville, Va.) in 200 μl of PKC kinase buffer to test the ability of these PKC isoforms to phosphorylate a final concentration of 0.025 mg/ml myelin basic protein (Sigma Aldrich). The PKC kinase buffer consisted of 20 mM Tris-HCl (pH 7.5), 6 mM magnesium acetate, phosphatidylserine (5 μg, 20 μl of 10 mg/ml solution), ATP (0.0045 mg/ml) and ICA-1 (10 uM and 50 uM). Basal kinase activity was measured in the absence of phospholipids. The reaction was terminated after incubation for 5 min at 30° C. by addition of sample loading buffer. Samples were then separated by PAGE and immunoblotted for either PKCiota or PKCzeta and phospho-myelin basic protein or normal myelin basic protein. The signal obtained was visualized using enhanced chemiluminescence (ECL; Amersham, Piscataway, N.J.).

Figure 3A:
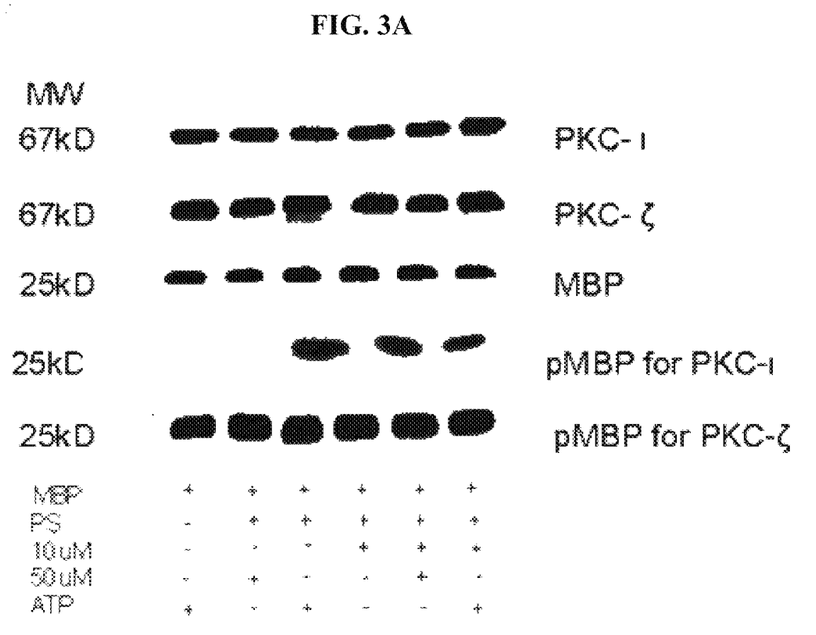
Figure 3B:
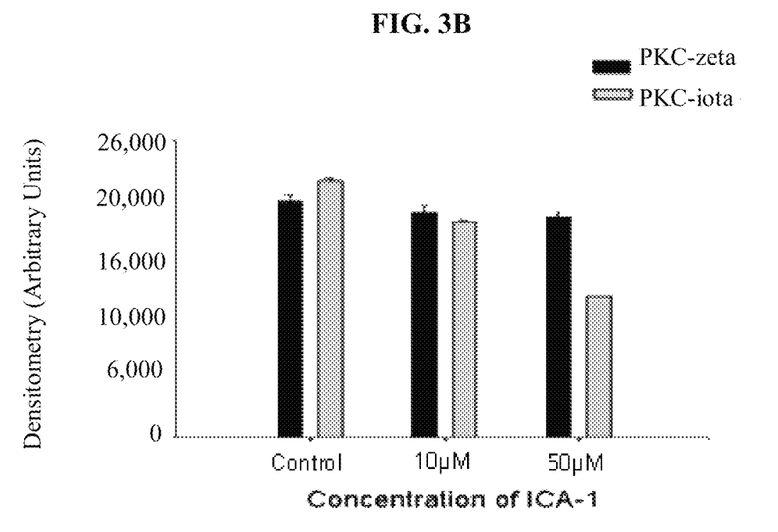

ICA-1 was incubated with either purified PKCiota or PKCzeta, myelin basic protein and a kinase activity assay was performed. Kinase activity assay was measured by Western blot analysis and antibodies against phospho-PKCiota phospho-PKCzeta and phospho-myelin basic protein (FIG. 3). Western blot analysis of either purified PKCiota or PKCzeta incubated in the absence of phosphatidylserine show no atypical PKC autophosphorylation or myelin basic protein phosphorylation. The absence of atypical PKC autophosphorylation and myelin basic protein phosphorylation in this control indicates that phosphatidylserine is essential for the activation of atypical PKCs in the kinase activity assay. Furthermore, incubation of purified PKCiota or PKCzeta in the presence of myelin basic protein and phosphatidylserine resulted in atypical phosphorylation of myelin basic protein. These results provide direct evidence that the PKC activity assay is functional. Next, the inhibitory action of ICA-1 on atypical PKC autophosphorylation and myelin basic protein phosphorylation was assessed in PKC activity assays to confirm that ICA-1 would block their phosphorylation. Treatment of either purified PKCiota and myelin basic protein with ICA-1 (50 µM) abrogated PKCiota induced myelin basic protein phosphorylation (P<0.002). Collectively, these results confirm that ICA-1 is an PKCiota inhibitor in-vitro.

Example IV

ICA-1 Reduces the Cell Proliferation in Neuroblastoma Cell Line BE(2)-C

Cells were cultured (5×104) in 25 cm2 tissue culture flasks. Twenty-four hours post plating, fresh media was supplied and cells were incubated with either equal volume of sterile water (vehicle control) or ICA-1 (40 nM to 100 nM). Cell viability was determined over a time period of 24, 48 and 72 hours. Following the initial exposure to ICA-1 no additional ICA-1 was supplied during the three day incubation period. At the specific time points, cells were washed with phosphate buffered saline (PBS), trypsinized and resuspended in 3 mL of PBS. Cell viability was quantified using trypan blue exclusion assay. A hundred microliter of the cell suspension was added to 25 µl of trypan blue and the numbers of unstained and stained cells were counted. A paired t-test was performed to test the statistical significance of the data.

Figure 4:
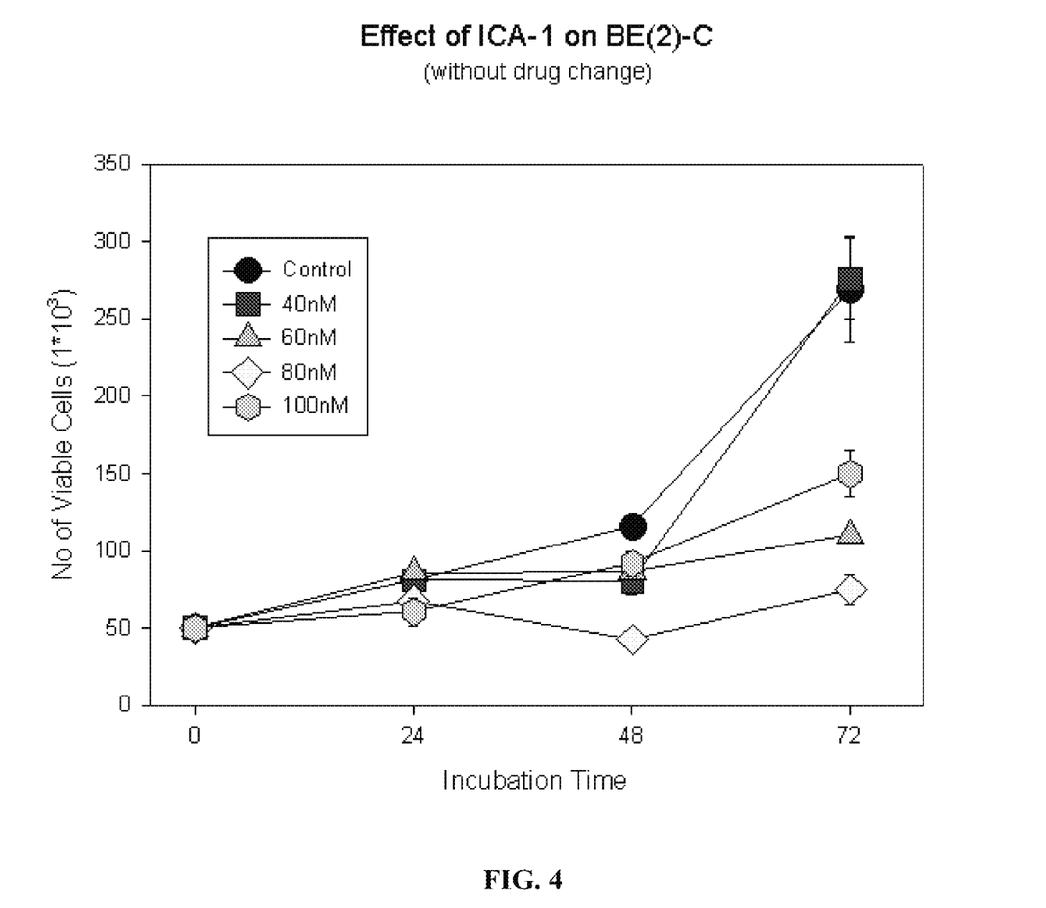
FIG. 4. Cell viability assay: Cells were cultured (5×104) in 25 cm2 tissue culture flasks. Twenty-four hours post plating, fresh media was supplied and cells were incubated with either equal volume of sterile water (vehicle control) or ICA-1 (40 nM to 100 nM). Cell viability was determined over a time period of 24, 48 and 72 hour using trypan blue exclusion assay (P value<0.05).

In BE(2)-C neuroblastoma cells low concentrations of ICA-1 (100 nM) significantly reduced the cell proliferation (P=0.037 at 24 h, P=0.0006 at 48 h and P=0.0058 at 72 h; paired T-test (FIG. 4). In addition, lower concentrations of ICA-1 (60 nM and 80 nM) were more effective in inhibiting the proliferation of BE(2)-C neuroblastoma cell (64% decrease and 53% decrease at 72 h, respectively (FIG. 4). These results indicate that ICA-1 is effective in inhibiting the proliferation of BE(2)-C neuroblastoma cells at very low concentrations.

Example V

ICA-1 Reduces the Expression of PKCiota in BE(2)-C Cells

BE(2)-C cells were cultured (1.5×105) in 75 cm2 tissue culture flasks. For Single ICA-1 treatment, twenty-four hours post plating, fresh media was supplied and cells were incubated with either equal volume of sterile water (vehicle control) or ICA-1 (80 nM). For Multiple ICA-1 treatment, twenty four hour post plating fresh media was supplied and cells were incubated with either equal volume of sterile water (vehicle control) or ICA-1 (80 nM). This was followed by addition of ICA-1 (80 nM) every twenty four hour. Total cell-lysates were prepared over a time period of 24, 48 and 72 hour and these were subjected to Western blot analysis for PKCiota.

Figure 5A:
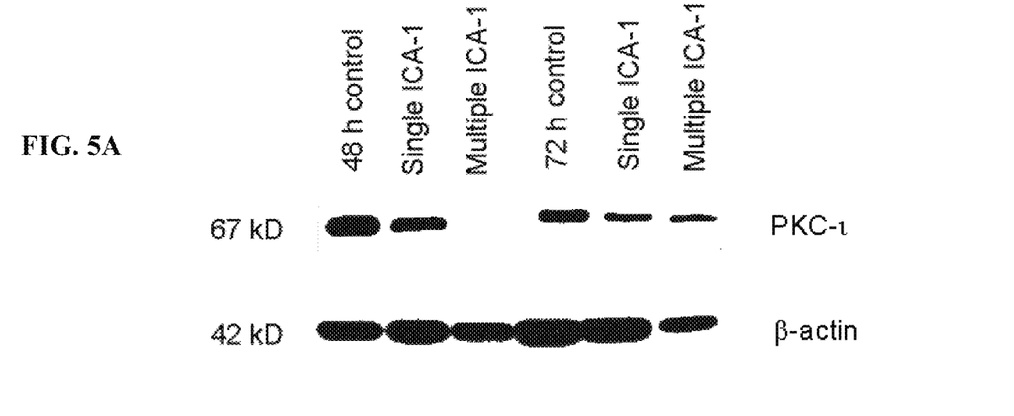
Figure 5B:
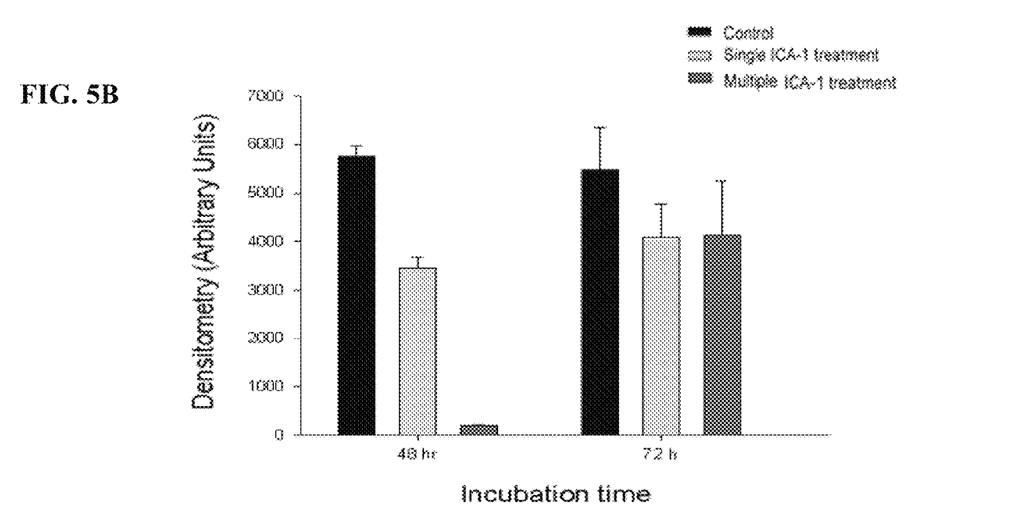

The treatment of BE(2)-C cells with ICA-1 (40 nM-100 nM) reduced the expression of PKCiota. An IC50 of 80 nM was obtained for 48 hour (FIG. 5). The result was more consistent for cells that were subjected to no supply of serum post treatment. Also multiple treatments (addition of the drug for every 24 hour) was more effective as compared to single treatment.

Example VI

The Decrease in PKCiota Expression on Treatment of ICA-1 is Independent of the Proteosome Degradation BE(2)-C cells were cultured (1.5×105) in 75 cm2 tissue culture flasks. For Single ICA-1 treatment, twenty-four hours post plating, fresh media was supplied and cells were incubated with either equal volume of sterile water (vehicle control) or ICA-1 (80 nM) and MG 115 (350 nM). For Multiple ICA-1 treatment, twenty four hour post plating fresh media was supplied and cells were incubated with either equal volume of sterile water (vehicle control) or ICA-1 (80 nM) and MG 115 (350 nM). This was followed by addition of ICA-1 (80 nM) every twenty four hours. Total cell-lysate were prepared over a time period of 24, 48 and 72 hour and these were subjected to Western blot analysis for PKCiota Cells were cultured ($5 \times 10^4$) in 25 cm2 tissue culture flasks. Twenty-four hours post plating, fresh media was supplied and cells were incubated with either equal volume of sterile water (vehicle control) or ICA-1 (40 nM to 100 nM). Cell viability was determined over a time period of 24, 48 and 72 hour using trypan blue exclusion assay (P value<0.05).

Figure 6:
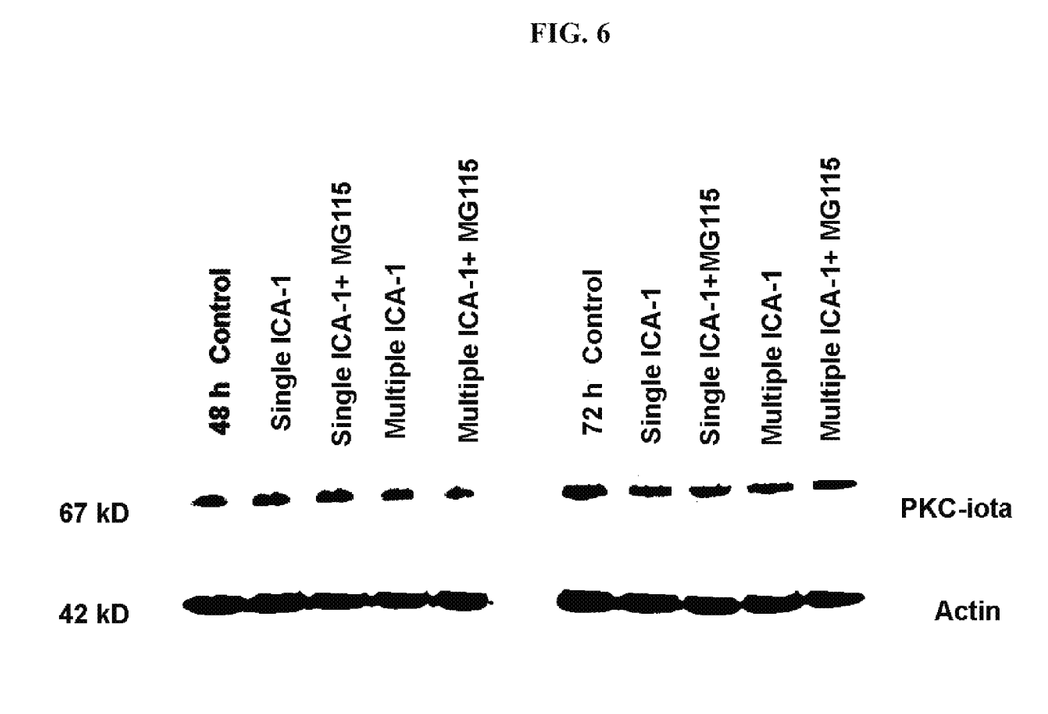

The ubiquitin-proteosome pathway plays a vital role in regulating the cellular levels of various PKC isoforms. To determine whether the reduction in the expression of PKCiota by ICA-1 is due to proteosome degradation, we performed ICA-1 treatment in presence of the proteosome inhibitor MG-115(FIG. 6). The data obtained was identical to the ICA-1 treatment in the absence of MG-115. Altogether it suggests that the reduction in the PKCiota levels is not due proteosomal degradation of PKCiota. The fact that the ubiquitin-proteosome pathway is not playing a role in the regulation of the PKCiota levels suggests that the reduction in PKCiota could be due to factors at the mRNA level.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating neuroblastoma, comprising administering to a subject in need of such treatment a therapeutically effective amount of 1H-imidazole-4-carboxamide, 5-amino-1-[2,3-dihydroxy-4-[(phosphonooxy)methyl]cyclopentyl]-[1R-(1α,2β,3β,4α)] (ICA-1).

2. The method of claim 1, wherein the therapeutically effective amount is between about 40 nM and 100 nM.

3. The method of claim 1, wherein ICA-1 is administered about every 24 hours.

4. A method of inhibiting the expression of protein kinase C-iota (PKCiota) in a neuroblastoma cell, comprising the step of contacting the neuroblastoma cell with a therapeutically effective amount of 1H-imidazole-4-carboxamide, 5-amino-1-[2,3-dihydroxy-4-[(phosphonooxy)methyl]cyclopentyl]-[1R-(1α,2β,3β,4α)] (ICA-1).

5. The method of claim 4, wherein the therapeutically effective amount is between about 40 nM and 100 nM.

6. The method of claim 4, wherein ICA-1 is administered about every 24 hours.

* * * * *

UNITED STATES PATENT AND TRADEMARK OFFICE
CERTIFICATE OF CORRECTION

PATENT NO. : 8,461,192 B2
APPLICATION NO. : 12/210576
DATED : June 11, 2013
INVENTOR(S) : Mildred Acevedo-Duncan et al.

It is certified that error appears in the above-identified patent and that said Letters Patent is hereby corrected as shown below:

In the Specification

Column 1,
Line 33, "apotential" should read --a potential--.

Column 3,
Line 8, "flasks For Single" should read --flasks. For Single--.
Lines 20-21, "treated with with ICA-1" should read --treated with ICA-1--.
Line 35, "cell-lysate were prepared" should read --cell-lysates were prepared--.
Line 36, "and 72 hour" should read --and 72 hours--.
Line 37, "PKCiota Cells" should read --PKCiota. Cells--.
Line 42, "72 hour using" should read --72 hours using--.

Column 4,
Line 1, "(every 24 hour)" should read --(every 24 hours)--.
Line 17, "surprising an unexpected" should read --surprising and unexpected--.

Column 5,
Line 21, "Unique a PKCiota" should read --a unique PKCiota--.

Column 6,
Line 20, "5% CO2" should read --5% $CO_2$--.
Line 34, "were no undergoing" should read --were not undergoing--.

Column 7,
Line 15, "is an PKCiota" should read --is a PKCiota--.
Line 32, "microliter of the" should read --microliters of the--.

Signed and Sealed this
First Day of October, 2013

Teresa Stanek Rea
*Deputy Director of the United States Patent and Trademark Office*

Column 8,
Line 4, "every twenty four hour" should read --every twenty four hours--.
Lines 5-6, "72 hour" should read --72 hours--.
Line 13, "24 hour)" should read --24 hours)--.
Line 32, "72 hour" should read --72 hours--.
Line 33, "PKCiota Cells" should read --PKCiota. Cells--.
Line 38, "72 hour" should read --72 hours--.
Lines 47-48, "is not due proteosomal" should read --is not due to proteosomal--.

SEQUENCE LISTING

<160> NUMBER OF SEQ ID NOS: 1

<210> SEQ ID NO 1
<211> LENGTH: 7
<212> TYPE: PRT
<213> ORGANISM: Homo sapiens

-continued

```
<400> SEQUENCE: 1

Gln Ile Arg Ile Pro Arg Ser
1               5
```